United States Patent [19]

Dombek

[11] Patent Number: 4,592,870

[45] Date of Patent: Jun. 3, 1986

[54] PRODUCTION OF METHYL ESTERS AND ETHYLENE GLYCOL ESTERS FROM REACTION OF CARBON MONOXIDE AND HYDROGEN IN PRESENCE OF RUTHENIUM CATALYST

[75] Inventor: Bernard D. Dombek, Charleston, W. Va.

[73] Assignee: Union Carbide Corporation, Danbury, Conn.

[21] Appl. No.: 319,887

[22] Filed: Nov. 10, 1981

Related U.S. Application Data

[63] Continuation of Ser. No. 971,667, Dec. 21, 1978, abandoned.

[51] Int. Cl.[4] .......................... C09F 5/08; C07C 67/08
[52] U.S. Cl. .......................... 260/410.6; 260/410.9 R; 518/700; 560/100; 560/103; 560/105; 560/112; 560/123; 560/232; 560/263; 560/265
[58] Field of Search ............... 560/103, 100, 112, 105, 560/232, 123, 263, 265; 260/410.6, 410.9 R; 518/700

[56] References Cited

U.S. PATENT DOCUMENTS

| | | |
|---|---|---|
| 2,534,018 | 12/1950 | Gresham et al. . |
| 2,535,060 | 12/1950 | Gresham . |
| 2,549,470 | 4/1951 | Howk et al. . |
| 2,636,046 | 4/1953 | Gresham . |
| 3,579,566 | 5/1971 | Fenton . |
| 3,833,634 | 9/1974 | Pruett et al. .................... 260/449 R |
| 3,944,588 | 3/1976 | Kaplan . |
| 3,965,192 | 6/1976 | Booth .................................. 568/454 |
| 4,170,605 | 10/1979 | Williamson et al. . |

FOREIGN PATENT DOCUMENTS 2644185 4/1977 Fed. Rep. of Germany .

OTHER PUBLICATIONS

Roy L. Pruett, "Industrial Organic Chemicals Through Utilization of Synthesis Gas", Annals of the New York Academy of Sciences, vol. 295, pp. 239–248 (1977).

G. Jenner et al., "Liquid Phase CO—$H_2$ Reactions in Presence of Ruthenium Catalysts", React. Kinet. Catal. Lett., vol. 15, 103–112 (1980).

Primary Examiner—Howard T. Mars
Attorney, Agent, or Firm—Steven T. Trinker

[57] ABSTRACT

This invention produces methyl esters and ethylene glycol esters by reacting carbon monoxide and hydrogen in a homogeneous liquid phase mixture containing a ruthenium carbonyl complex catalyst and an acyl compound. Methyl ester and ethylene glycol ester are the predominant products. These esters are used as precursors in the formation of ethylene glycol, vinyl acylates such as vinyl acetate, ethylene oxide, ethylene carbonate and methanol.

2 Claims, No Drawings

4,592,870

PRODUCTION OF METHYL ESTERS AND ETHYLENE GLYCOL ESTERS FROM REACTION OF CARBON MONOXIDE AND HYDROGEN IN PRESENCE OF RUTHENIUM CATALYST

This application is a continuation of our prior U.S. application Ser. No. 971,667 filed Dec. 21, 1978, now abandoned.

GENERAL DESCRIPTION OF THE INVENTION

This invention is directed to producing methyl esters and ethylene glycol esters from mixtures of carbon monoxide and hydrogen. The process of this invention involves the reaction of mixtures of carbon monoxide and hydrogen, such as synthesis gas, in a homogeneous liquid phase mixture which comprises an acyl compound and a ruthenium carbonyl complex. The process is conducted at a temperature of between about 50° C. and about 400° C. and at a pressure between about 500 psia and about 12,500 psia for a period of time sufficient to produce methyl ester and ethylene glycol ester as the predominant products.

DISCUSSION OF THE PRIOR ART

Pruett and Walker, U.S. Pat. No. 3,833,634, patented Sept. 3, 1974, based on an application originally filed Dec. 21, 1971, describe a process for preparing glycols by reacting an oxide of carbon with hydrogen using a rhodium carbonyl complex catalyst. The patent describes at column 5, lines 65-72, that the reaction can be effected in the presence of a reactive diluent such as acetic acid and alkanols to produce, respectively, glycol esters and glycol ethers. The examples of the patent compare the reaction of mixtures of hydrogen and carbon monoxide in the presence of the desired rhodium catalyst with other metals. In Example 9 of the patent, the reaction was attempted with triruthenium dodecacarbonyl as the catalyst and no polyhydric alcohol product was obtained. Gresham, U.S. Pat. No. 2,535,060, claims a process for preparing monohydric alcohols by introducing carbon monoxide, hydrogen and a hydroxylated solvent in the presence of a ruthenium-containing substance and an alkaline reagent which controls the PH within the range of 7 to 11.5 at a temperature within the range of 150° to 300° C. under a pressure within the range of 200 to 1,000 atmospheres.

Example 1 of the Gresham patent uses ruthenium dioxide as the precursor to the ruthenium catalyst. At column 2, lines 30-33 of the patent, the patentee states his belief that ruthenium dioxide is reduced in situ during the reaction. Example 1 compares the use of a number of solutes such as phosphoric acid, acidic phosphate buffer, no solutes at all, ammonia, sodium bicarbonate sodium formate, sodium hydroxide and potassium bicarbonate. In this example, the solvent was water. In Example 2 of Gresham, a number of alcohols were characterized as solvents.

Gresham's work should be contrasted with his earlier work described in U.S. Pat. No. 2,636,046, filed Oct. 16, 1948. In this patent, Gresham describes the production of polyfunctional oxygen-containing organic products including such compounds as ethylene glycol, glycerine, and the like. This is accomplished by the reaction of hydrogen with carbon monoxide in the presence of a carboxylic acid such as acetic acid to produce the corresponding glycol acetate. According to this patent, the reaction of carbon monoxide with hydrogen must be at pressures of above 1,000 atmospheres and "particularly above a minimum of about 1,400 atmospheres in order to obtain the polyfunctional oxygen-containing organic compounds". The patent specifically states at column 2, lines 37-43 that "[I]n the hydrogenation of oxides of carbon at pressures of 1,000 atmospheres and below, virtually no polyfunctional compounds are produced. At pressure above 1,000 atmospheres and especially at pressures of about 1,500 to 5,000 atmospheres preferably 2,000 to 5,000 atmospheres, polyfunctional compounds are obtained". Though the examples of the patent describe the use of only cobalt catalyst, the patentee, at column 3, line 61, indicates that the catalyst may contain "cobalt, ruthenium, etc." According to the patentee, the most outstanding results are obtained by using a catalyst containing cobalt, especially compounds of cobalt which are soluble in at least one of the ingredients of the reaction mixture.

According to Roy L. Pruett, *Annals, New York Acadamy of Sciences*, Vol. 295, pages 239-248 (1977), at page 245, metals other than rhodium were tested to determine the production of ethylene glycol from mixtures of carbon monoxide and hydrogen. These metals included cobalt, ruthenium, copper, manganese, iridium and platinum. Of these metals, only cobalt was found to have a slight activity, citing British Pat. No. 665,698 which corresponds to the last mentioned Gresham U.S. Patent. Pruett stated that such slight activity with cobalt was "qualitatively" in agreement with the results obtained by Ziesecke, 1952, Brennstoff-Chem. 33:385.

Prior to the filing of U.S. Pat. No. 2,535,060 and subsequent to the filing of U.S. Pat. No. 2,636,046, there was filed on Apr. 12, 1949 a commonly assigned application by Howk, et al. which issued as U.S. Pat. No. 2,549,470 on Apr. 17, 1951. The Howk, et al. patent is directed to a catalytic process for making monohydric straight chain alcohols. The patent emphasizes the production of straight chain primary hydroxyalkanes having from 3 to 50 or more carbon atoms in the molecule. This, the patent states, is accomplished by introducing hydrogen, carbon monoxide and a hydroxylated solvent into a reaction vessel, and heating the mixture in the presence of a catalyst of the class consisting of ruthenium metal, ruthenium oxide and ruthenium carbonyl, at a pressure within the range of 200 to 1000 atmospheres and at a temperature within the range of 100° to 250° C. The liquid hydroxyl-containing reaction medium may be water or alcohol, preferably a primary hydroxyalkane having from 1-10 carbon atoms per molecule. According to the patentee, a substantial proportion of the reaction product usually consists of alcohol containing more than 6 carbon atoms per molecule. The patent goes on to state-". . . the reaction products usually contain virtually no hydrocarbons, acids, esters or branched-chain alcohols. These results were entirely unexpected, in view of the existing knowledge of the catalytic reaction between carbon monoxide and hydrogen in the presence of alcohols and Group VIII metal catalysts."

According to the Howk, et al. patent

"It should be emphasized here that, under the conditions of temperature, pressure and gas ratios just described, no reaction takes place between carbon monoxide and hydrogen in a liquid medium (water or alcohol) if one of the common group VIII metels, such as cobalt or nickel, is used as the catalyst. This is evidenced by the fact that, using, for example, a cobalt catalyst, no significant drop in pressure is observed when carbon monoxide and hydrogen are contacted under the conditions recited. Ruthenium is thus unexpectedly different from these related metals."

The numbered examples indicate an apparent preference for making normal-monohydric alcohols, with the proportion of pentane soluble to pentane insoluble alcohol being at least 2:1. In one example, starting at the bottom of column 6 of Howk, et al., the solvent employed is characterized as a carboxylic acid or anhydride rather than the neutral hydroxylated solvents which were described in the other examples. This comparative example demonstrated that in a process operated at 200° C. for 18 hours using pressures maintained in the range of 300–950 atmospheres by repressurizing periodically with synthesis gas, there was produced a reaction product containing "a large quantity of wax." According to the author, 40.55 parts of esters boiling from 59° C. at atmospheric pressure to 150° C. at 116 millimeters pressure were obtained and this can be compared to the wax obtained in the amount of 37.06 parts. In that Particular example, the patentee appears to have demonstrated that when one does not employ the hydroxylated solvent, the amount of wax essentially equals the amount of pentane soluble alcohol products obtained.

At column 3, lines 54 et seq., Howk, et al. describe the influence that pressure has on the course of the reaction. According to Howk, et al. with pressures up to about 150 atmospheres the reaction products are only hydrocarbons. This appears to be in accord with recent work described by Masters, et al. in German Patent Application (Offenlegungschrift) 2,644,185, based upon British priority application Specification No. 40,322-75, filed Feb. 10, 1975. Masters, et al. obtained only hydrocarbons at such pressures using a ruthenium catalyst.

Fenton, U.S. Pat. No. 3,579,566, patented May 18, 1971, is concerned with a process of reducing organic acid anhydrides with hydrogen in the presence of a Group VIII noble metal catalyst and a biphyllic ligand of phosphorus, arsenic or antimony. The process of Fenton bears a remarkable similarity to oxo processing conditions to produce aldehydes and alcohols (compare with Oliver, et al. U.S. Pat. No. 3,539,634 patented Nov. 10, 1970) except that Fenton fails to supply an olefinic compound to the reaction. In the Fenton reaction, an acid anhydride, such as acetic acid anhydride, is reduced to ethylidene diacetate in the presence of hydrogen and a rhodium halide or a mixture of palladium chloride and ruthenium trichloride catalyst, provided in combination with triphenylphosphine. Ethylene glycol diacetate is also observed. Carbon monoxide is added in the examples of Fenton which is described by Fenton, at col. 2, lines 48–51 as follows: "If desired, a suitable inert gas, such as carbon monoxide can also be charged to the reaction zone...". (Emphasis added). Of particular significance is the fact that none of Fenton's examples produce a methyl ester, as are produced by the process of this invention. Another point is that Fenton's ethylidene diacetate can be thermally cracked to produce vinyl acetate, see col. 1, lines 42–44. It would seem that such occurred in example 1 of Fenton and acetic acid added to the vinyl acetate to form ethylene glycol diacetate.

The following is believed to be a fair analysis of the aforementioned references, i.e., what they teach one skilled in the art and the direction that they could lead one in pursuit of whatever is their objectives:

(1). Gresham, U.S. Pat. No. 2,636,046 states that at exceedingly high pressures in excess of 1500 atmospheres, that is in excess of about 1550 kg/cm$^2$, one can produce some glycol acetates by the reaction of carbon monoxide and hydrogen in the presence of acetic acid utilizing, most desirably, a cobalt catalyst although some undescribed ruthenium compound can be substituted for cobalt.

(2). The Pruett and Walker patent shows in examples 9 and 17 at columns 11 and 12, respectively, that the reaction of CO and H$_2$ in the presence of ruthenium carbonyl and cobalt carbonyl complexes operated at about 20–24,000 pounds/in$^2$. (1400–1700 kg/cm$^2$) pressure will, in the case of ruthenium, produce no polyhydric alcohols and, in the case of cobalt, produce trace amounts of mono and diacetates of ethylene glycol. Thus, with respect to the cobalt catalyst a minimum pressure of about 20,000 psi (1400 kg/cm$^2$) seems to be needed to make any glycol compound. In the case of ruthenium, the pressure at which glycol can be made from CO and H$_2$ had not been defined. (3). Howk et al. (U.S. Pat. No. 2,549,470) who employ a lower pressure reaction than Gresham, produce only monohydric alcohols from the reaction of CO and H$_2$ using a ruthenium catalyst. The maximum pressure for the Howk, et al., process is about 1000 atmospheres. The reaction produces a spectrum of monohydric alcohols ranging from methanol to very high molecular weight alcohols, some alcohols containing up to 40 carbon atoms. The products are classified as pentane soluble materials and pentane insoluble materials. The pentane insoluble higher alcohols are characterized as waxes and less desirable than the pentane soluble alcohols. When Howk, et al. ran the reaction in acetic acid at a pressure ranging from 300 to 950 atmospheres, there was produced "a large quantity of wax together with a liquid." The amount of wax was essentially the same amount, in parts by weight, as ester products, assumed to be esters of monohydric alcohols.

(4) The second Gresham U.S. Pat. No. 2,535,060) appears to be an improvement on the Howk et al. patent. It teaches the desirability of controlling the pH of the reaction medium in the reaction between carbon monoxide and hydrogen in the presence of a ruthenium-containing catalyst such as described by Howk, et al. The presence of trace amounts of carboxylic acid is considered very undesirable by Gresham. Gresham states that traces of carboxylic acids produce an acidity which "has a very profound effect upon the subsequent course of the reaction, causing the formation of relatively longer chain products, such as waxy alcohols containing up to 50 or more carbon atoms per molecule (c.f. copending application of Hager and Howk, Ser. No. 87,114, filed Apr. 12, 1949). If the pH is more strongly acidic, high molecular weight waxy products are formed in still greater proportions." The co-pending application referred to is the Howk, et al. U.S. Pat. No. 2,549,470, mentioned previously. Thus, Gresham specifies that it is desirable to maintain the pH of the reaction solution alkaline in order to obtain a better distribution of straight chain mobnohydric primary alcohols. According to Gresham, the quantity of methanol formed in his reaction "is extremely small" (see column 1, line 49). (5) There is apparently a minimum pressure according to Howk, et al used to avoid the formation of hydrocarbons and this appears to be supported by the disclosure of Masters, et al., supra. (6) Fenton utilized rhodium, palladium and ruthenium halides in the presence of a mixture of hydrogen and carbon monoxide and an acid anhydride, and recognized only the reduction of the anhydride.

THE INVENTION

The process of this invention involves the manufacture of esters of methanol and ethylene glycol. These esters are used as precursors in the formation of ethylene glycol, vinyl acylates such as vinyl acetate, ethylene oxide, ethylene carbonate and methanol. These esters of methanol and ethylene glycol are produced by the reaction of carbon monoxide and hydrogen in a homogenous liquid phase mixture comprising a ruthenium carbonyl complex and an acyl compound, at a temperature of between about 50° C. and about 400° C. and at a pressure between about 500 psia and about 12,500 psia for a period of time sufficient to produce such esters as the predominant products.

This invention is distinguishable from the Gresham (U S. Pat. No. 2,636,046) since the present process is operated at significantly lower pressures than the 1500 atmospheres (22,050 psia) described by Gresham. The process of this invention produces little, if any, of the wax materials which are described by Howk, et al. and produces a product not described by Howk, et al., that is, ethylene glycol esters. The process of this invention is also capable of producing glycerine esters and some alkyl acylates The alkyl groups contain the same number of carbon atoms as are contained in the acyl moiety added to the reaction, because it is made by reducing the acyl moiety to alkanol, which condenses with unreduced acyl compound to produce the ester.

The process of this invention involves providing carbon monoxide and hydrogen within a homogeneous liquid phase mixture. This mixture contains an acyl compound and a ruthenium carbonyl complex as the essential components of the mixture. Other materials can be contained in the mixture without deviation from the process of this invention.

The catalyst of this invention is a ruthenium compound which contains a carbonyl directly bonded to ruthenium. The ruthenium compound which is provided to the reaction is not necessarily in a form which will effectively catalyze the reaction. Ruthenium compounds, such as ruthenium salts and oxides, may be introduced to the reaction in a condition which allows them to be solubilized, and under the conditions of the reaction they are converted into a carbonyl complex which effectively catalyzes the reaction. The composition and structure of the ruthenium carbonyl complex which catalyzes the desired reaction is not specifically known. It may be a monoruthenium or polyruthenium compound. Illustrative of polyruthenium compounds are the well-known cluster compounds of ruthenium. Essential factors in achieving the catalyst are the temperature and pressure conditions that one employs.

The ruthenium-containing substances which may be employed in the practice of this invention encompass those which are described, for example, in Gresham, U.S. Pat. No. 2,535,060 at column 2, starting at line 38 to line 48. It is not advisable to place ruthenium compounds or substances on a support material for use in the process of this invention because there are no benefits compared with solubilizing such ruthenium compounds in combination with the aforementioned acyl compound. Moreover, ruthenium deposited on a support material can be expected to be solubilized in a homogenous liquid phase reaction system as it is contacted with carbon monoxide. Even ruthenium metal in the presence of an acyl compound, carbon monoxide and hydrogen can be converted to a ruthenium carbonyl complex which is soluble in the acyl compound or the acyl compound in combination with one or more other solvents. Ruthenium oxides, such as the dioxide, sesquioxide, or tetraoxide are capable, under appropriate conditions, of being solubilized and converted to a carbonyl complex which can be used to form the catalyst under the conditions of this process. Ruthenium carbonyl compounds (which include ruthenium carbonyl hydrides) are already provided with a carbonyl group, and under the conditions of the reaction, can be sufficiently changed to achieve the desired catalytic effect. Ruthenium salts such as those of organic acids can be employed in the practice of this invention to produce the catalyst. However, ruthenium chloride, ruthenium bromide and ruthenium iodide directly added to the reaction system are not desirable in the practice of this invention. However, if the ruthenium halide is treated with an appropriate base provided in amounts which are at least stoichiometrically equivalent to the halogen present in the ruthenium halide, then the resulting ruthenium compounds, when separated from the halide salt, can be employed in the process of this invention. In addition to those ruthenium compounds described in the aforementioned Gresham patent, one may employ ruthenium salts of bidentate ligands, allyl complexes, arene complexes, and alkyl complexes. The choice of ruthenium compounds is varied and not critical to this invention. A number of ruthenium complexes are known to be more stable to the presence of carbon monoxide than other ruthenium compounds and the skilled worker can determine which particular ruthenium compound might take longer to initiate a reaction than other rutheni.um compounds. On that basis, one can select the particular ruthenium compound to be utilized in forming the catalyst. However, ruthenium which is associated with an organic molecule or complexed with carbon monoxide is most readily solubilized so as to provide the ruthenium catalyst of this process.

The quantity of the ruthenium catalyst which is employed is not narrowly critical and can vary over a wide range. In general, the process of this invention is desirably conducted in the presence of a catalytically effective quantity of the active ruthenium species which gives a suitable and reasonable reaction rate. The reaction proceeds when one employs as little as about $1 \times 10^{-6}$ weight percent, or even a lesser amount of ruthenium (calculated as the metal in the complex catalyst) based on the total quantity of reaction mixture. The upper concentration of the ruthenium catalyst can be quite high, e.g., about twenty weight percent of ruthenium based on the total quantity of reaction mixture. Higher concentrations may be used if desired. However, the upper concentration appears to be dictated by economics in terms of the cost of the ruthenium to achieve the given reaction and ease of handling of the homogenous phase reaction mixture during the course of the reaction. Depending on various factors, such as the acyl compound of choice, the partial pressures of carbon monoxide and hydrogen, the total operative pressure of the system, the operative temperature, the choice of solvent, if any, and other considerations, a concentration of between about $1 \times 10^{-5}$ and about 20 weight percent ruthenium (contained in the complex catalyst) based on the total quantity of the homogenous liquid phase reaction mixture is generally suitable in the practice of this invention.

Acyl compounds which may be used in the practice of the process of this invention are not a critically limited class of compounds They include saturated carboxylic acids such as saturated aliphatic monocarboxylic acids containing 1 to about 20 carbon atoms; saturated cycloaliphatic carboxylic acids containing at least 4 carbon atoms in the cycloaliphatic group; aromatic monocarboxylic acids wherein the aromtaic group contains 6 or more carbon atoms; alkaryl monocarboxylic acids wherein the alkyl group therein contains from 1 to about 20 carbon atoms and the aryl moiety contains 6 or more carbon atoms; aralkyl carboxylic acids wherein the aryl group thereof contains 6 or more carbon atoms and the alkyl moiety contains from 1 to about 20 carbon atoms, and the like. Illustrative of suitable saturated aliphatic carboxylic acids are acetic acid, propionic acid, n-valeric acids, isovaleric acid, pivalic acid, the hexanoic acids, the heptanoic acids, the octanoic acids, the nonanoic acids, the decanoic acids, and the remaining saturated carboxylic acids in the fatty acid series, such as stearic acid, eicosanoic acid, and the like. Illustrative of suitable aromatic carboxylic acids are benzoic acid, naphthoic acid (both isomeric species ), and the like. Illustrative of suitable alkaryl carboxylic acids are 4-methylbenzoic acid, 3,4-dimethylbenzoic acid, 4-octylbenzoic acid, 4- octadecanyl benzoic acid, and the like. Illustrative of suitable aralkyl carboxylic acids are phenylacetic acid, phenyl-8-octanoic acid, phenyl-18-stearic acid, and the like. Illustrative of suitable cycloaliphatic carboxylic acids are cyclohexane carboxylic acid, cyclobutane carboxylic acid, 2,2-dimethyl-1-cyclobutane carboxylic acid, cycloctane carboxylic acid, and the like. Also included as acyl compounds are the anhydrides of the aforementioned carboxylic acids. Extremely desirable anhydrides which may be used in the practice of this invention include acetic anhydride, propionic anhydride, benzoic anhydride, and the like. Mixtures of the aforementioned carboxylic acids or anhydrides and mixtures of the acids and anhydrides can be employed in the practice of this invention. Also included are anhydrides which are derived from two different acid moieties such as the anhydride of a mixture of acetic acid and propionic acid. Further included by the term acyl compounds are compounds from which the aforementioned carboxylic acids can be derived.

The amount of acyl compound provided in the homogenous liquid phase reaction mixture during the course of the reaction is an amount which is sufficient to produce a desired amount of ester products. The amount of acyl compound can be as low as a fraction of 1 percent of the weight of the homogenous liquid phase reaction mixture, or as high as the full weight of the solution provided to the reaction mixture less the weight of the ruthenium com-ponents therein.

The process of this invention is carried out in a homogenous liquid phase. It is desirable to employ a liquid which is characterized as a solvent to the extent that it will dissolve enough of the ruthenium catalytic species to effect the aforementioned reaction. The solvent should not prevent the formation of esters of ethylene glycol. The solvent may be the acyl compound as described above, or another material combined with the acyl compound and which in combination with the catalytic species provides the homogeneous liquid phase reaction mixture.

The solvent may be inert to the reactions which are taking place in the process, or may participate in these reactions in a homogeneous liquid phase reaction mixture to produce the desired ester. In some respects, the solvent may be a material which will react with another material in the mixture to form a third material which acts as a solvent. The solvent may also include the products of the reaction. Illustrative of solvents suitable for use in the practice of this invention are saturated and aromatic hydrocarbons, e.g., hexane, octane, dodecane, naphtha, decalin, tetrahydronaphthalene, kerosene, mineral oil, cyclohexane, cycloheptane, alkylcycloalkane, benzene, toluene, xylene, naphthalene, alkylnaphthalene, and the like; ethers such as tetrahydrofuran, tetrahydropyran, diethylether, 1,2-dimethoxybenzene, 1,2-diethoxybenzene, the mono- and dialkylethers of ethylene glycol, propylene glycol, butylene glycol, diethylene glycol, dipropylene glycol, oxyethylene oxypropylene glycol, and the like; alkanols such as methanol, ethanol, propanol, isobutanol, 2-ethylhexanol, and the like; ketones and aldehydes such as acetone, methyl ethyl ketone, acetaldehyde and the like; esters such as methyl acetate, propyl acetate, butyl acetate, methyl propionate, ethyl butyrate, methyl laurate, and the like; lactones, such as butyrolactone; water; fluorinated hydrocarbons that are inert under the reaction conditions such as perfluoro ethane, monofluorobenzene, and the like. Another class of solvents are sulfones such as dimethylsulfone, diethylsulfone, diphenylsulfone,sulfolane, and the like. Mixtures of the aforementioned solvents may be employed so long as they are compatible with each other under the conditions of the reaction and will adequately provide the homogenous liquid phase for carrying out the process of this invention. Of the aforementioned classes of solvents, the hydrocarbons, ethers, sulfones, and flourinated hydrocarbons are typically nert in the present process, whereas esters, water, alcohols, aldehydes and ketones will in one manner or another enter into a reaction during the course of the present process. The esters have the capability of entering into ester interchange reactions, the aldehydes and ketones into reduction reactions, the water into hydrolysis reactions, and the alcohol into alcohol interchange reactions with esters, or into esterification reactions with acyl compounds. In using alcohols as solvents, it must be recognized that since they are capable of reacting with the acyl compounds, they should be employed in a molar amount which is less than the molar amount of acyl compound provided in the reaction, leaving an amount of acyl compound in the reaction sufficient to effect the formation of the desired quantity of ester by the process of the present invention.

Preferably, the solvent is a mixture of an acyl compound and a co-solvent which in combination with the acyl compound increases the yield of ethylene glycol ester product.

The co-solvent which is used in the practice of this invention has a high dielectric constant, is weakly basic and is a good ionizing solvent. These co-solvents include sulfones such as sulfolane, phosphine oxides and lactones.

The term sulfolane as used herein is intended to cover tetramethylene sulfone and substituted tetramethylene sulfones which provide essentially the same advantages as a result of their solvent characteristics as tetramethylene sulfone. Illustrative of substituted sulfolanes which are of a kind that may be suitable as a co-solvent with the acyl compound in the practice of this invention are those which re characterized by the following formula:

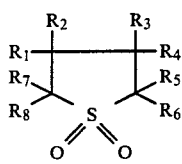

wherein each of $R_1$ through $R_8$ is at least one of hydrogen, hydroxyl, straight or branched chain alkyl, preferably having from 1 to 12 carbon atoms, most preferably 1 to 6 carbon atoms in the alkyl chain, such as methyl, ethyl, isopropyl, butyl, octyl, dodecyl and the like; a cycloaliphatic group including the monocyclic and bicyclic groups such as cyclopentyl, cyclohexyl, bicyclo [2.2.1] heptyl, and the like; or an aryl, alkaryl, or aralkyl group such as phenyl, naphthyl, xylyl, tolyl, benzyl, beta-phenylthyl and the like; an ether of the formula—$(O-R°)$ wherein $R°$ may be aryl or lower alkyl having from 1 to 12 carbon atoms, preferably 1 to 4 carbon atoms in the alkyl chain; an alkylene or polyalkylene ether of the formula—$(OC_nH_{2n})_x$—$OR^{\infty}$ wherein n has an average value of from 1 to about 4, x has an average value of from 1 to about 150, preferably 1 to about 20, most preferably 1 to about 4, and $R^{\infty}$ may be hydrogen or alkyl having from 1 to 6 carbon atoms in the alryl chain, such as poly (oxyethylene), poly(oxypropylene), poly(oxyethylene-oxypropylene), alkylene and polyalkylene glycols and lower alkyl ethers thereof; a carboxylate group of the formula:

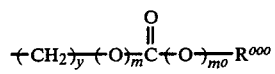

wherein y may have any value between 0 and 12, m and $m^o$ may be zero or one provided that when either m or $m^o$ is one the other is zero, and $R^{ooo}$ may be a lower alkyl group having from 1 to 12 carbon atoms, preferably from 1 to 4 carbon atoms, or aryl; provided that not all of the $R_{1-8}$'s are hydrogen.

Illustrative of the phosphine oxide compounds which are suitable in the practice of this invention are those which are characterized by the following formulae:

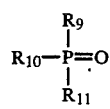
I.

wherein $R_9$, $R_{10}$ and $R_{11}$ are independently:

(1) straight or branched chain alkyl having 1 to 20 carbon atoms, preferably having 1 to 12 carbon atoms, most preferably 1 to 6 carbon atoms, such as methyl, ethyl, isopropyl, butyl, octyl, dodecyl, octadecyl and the like;

(2) substituted alkyl wherein the substituents may be:
(i) fluorine, such as in $CF_3$,
(ii) those of the formula $-(O-R')$ wherein $R'$ may be hydrogen, aryl or lower alkyl having from 1 to 12 carbon atoms, preferably 1 to 4 carbon atoms,
(iii) those of the formulae—$(OC_aH_{2a})_bOR'$ or —$(OCHCH_3C_aH_{2a})_bOR'$ wherein a has an average value of from 2 to about 4, b has an average value of from 1 to about 1000 and $R'$ is as previously defined;

(3) a group of the formulae:

wherein c may have any value between 1 and 12, d and e may be zero or one provided that when either d or e is one the other is zero; $R_{12}$ is an alkylene or oxyalkylene radical having 1 to 12 carbon atoms or an arylene radical, $R_{13}$ is an alkyl radical having from 1 to 12 carbon atoms, preferably from 1 to 4 carbon atoms, or aryl;

(4) a cycloaliphatic group including the monocyclic and bicyclic groups such as cyclopropyl, cyclopentyl, cyclohexyl, bicyclo [2.2.1] heptyl, and the like;

(5) an aryl, alkyaryl, or aralkyl group which may be substituted by $R_1$ or by substituents (i) to (iii);

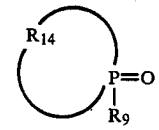

wherein $R_{14}$ is an alkylene radical of 3 to 20 carbon atoms or -0-alkylene- wherein the alkylene contains 3 to 20 carbon atoms which alkylene radicals may be substituted by $R_9$, wherein $R_9$ is a previously defined, or by an oxo group, or by substituents (i) to (iii).

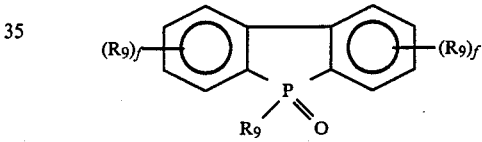
III.

wherein $R_9$ is as previously defined or one of substituents (i) to (iii) and f is 0 to 4.

The preferred phosphine oxides include

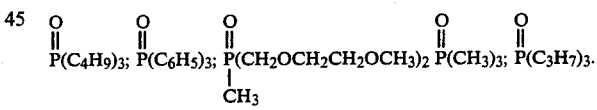

The lactones suitable for use herein include gamma-butyrolactone and delta-valerolactone as well as substituted gamma butyrolactone solvents of the formula:

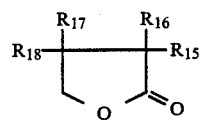

wherein $R_{15}$ through $R_{18}$ is at least one of hydrogen, straight or branched chain alkyl, preferably having from 1 to 12 carbon atoms, most preferably 1 to 6 carbon atoms in the alkyl chain, such as methyl, ethyl, isopropyl, butyl, octyl, dodecyl and the like; a cycloaliphatic group including the monocyclic and bicyclic groups such as cyclopentyl, cyclohexyl, bicyclo [2.2.1] heptyl, and the like; or an aryl, alkaryl, or aralkyl group such as phenyl, naphthyl, xylyl, tolyl, benzyl, betaphenylethyl and the like; an ether of the formula O—$R_{19}$) wherein $R_{19}$ may be aryl or lower alkyl having from 1 to 12 carbon atoms, preferably 1 to 4 carbon atom in the alkyl chain; and alkylene or polyalkylene ether of the formula $-(OC_hH_{2h})_w-OR_{20}$ wherein h has an average value of from 1 to about 4, w has an average value of from 1 to about 150, preferably 1 to about 20, most preferably 1 to about 4, and $R_{20}$ may be alkyl having from 1 to 6 carbon atoms in the alkyl chain, such as poly(oxyethylene), poly(oxypropylene), poly(oxyethylene-oxypropylene), alkyl ethers of alkylene and polyalkylene glycols;

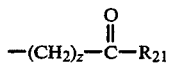

$$-(CH_2)_z-\overset{O}{\underset{\|}{C}}-R_{21}$$

wherein z may have any value between 0 and 12 and $R_{21}$ may be a lower alkyl group having from 1 to 12 carbon atoms, preferably from 1 to 4 carbon atoms, or aryl; provided that one of $R_{15}$ or $R_{16}$ is other than hydrogen.

Preferably, the substituted-gamma-butyrolactone solvent used in the practice of the present invention is 2,2-di(alkyl) substituted-gamma-butyrolactone, wherein the alkyl group contains 1 to 12 carbon atoms, and preferably 1 to 6 carbon atoms. The most preferred 2,2-di(alkyl)-gamma-butyrolactone solvent is 2,2-dimethyl-gamma-butyrolactone.

The process of this invention can be effected over a wide temperature range from moderate temperatures to elevated temperatures. In general, the process is conducted at a temperature of between about 50° C. and about 400° C. Operating the process at temperatures lower than 50° C. will not produce the desired products at an optimum rate so that the reaction will have to be operated over an extended period of time in order to obtain the desired product of reaction. When operating the process at temperatures higher than 400° C. there is a tendency for the reaction products and organic materials contained in the reaction mixture to decompose. Also there is a tendency for the catalytic species to decompose to insoluble ruthenium compounds. The formation of insoluble ruthenium compounds can be controlled by increasing the reaction pressure which is generally sufficient to keep the ruthenium catalytic species in solution. In most cases, when operating at the lower end of the temperature range, it is desirable to utilize pressures in the higher end of the pressure range. The preferred temperature range is between about 150° C. and 350° C., while the most preferred temperature range is between about 200° C. and 330° C. However, there are occasions when a preferred temperature range may include any of the more desirable ranges as well as the broadest range such that the process may be operated at a temperature of between 100° C. and 325° C. as well as between about 50° C. and 350° C.

The process of the present invention is effected under superatmospheric pressure conditions. Invariably, the pressure is produced by the hydrogen and carbon monoxide provided to the reaction. Pressures of between about 500 psia (36.535 kg/cm²) and about 12,500 psia (878.8 kg/cm²) represent an operative limit for producing the ester products. However, when operating the process at pressures at the lower end of the pressure range, the rates of reaction become markedly slow and therefore the reaction period must be extended until the desired amount of reaction product is produced. On the other hand, when the process is operated at a pressure near the high end of the range, the rate of production of the desired products will be increased. However, operating the process at pressures in excess of the upper end of the pressure range is not economically justified and according to the prior art literature would tend to result in a decrease in the rate of reaction. In the preferred practice of this invention, it is desirable to operate the process at a pressure of between about 2,500 psia (175.77 kg/cm²) and about 10,000 psia (703.07kg/cm²). In addition to the partial pressures exerted by carbon monoxide and hydrogen, a partial pressure will be exerted by inert gases, such as argon, if these are employed in the reaction The process of this invention is effected for a period of time sufficient to produce the desired ester products. In general the reaction time can vary from minutes to several hours, i.e., from a few minutes to approximately twenty four hours, and longer. If the more sluggish reaction conditions are selected, then the reaction time will have to be extended until the desired product is produced. It is readily appreciated that the residence period (i.e., time of reaction) will be influenced by the reaction temperature, concentration and choice of the ruthenium catalyst, total gas pressure, partial pressure exerted by its components, concentration and choice of solvent, the acyl compound and other factors. The synthesis of the desired products by the reaction of hydrogen, carbon monoxide and the acyl compound is suitably conducted under operative conditions which give reasonable reaction rates and/or conversions.

The relative amounts of carbon monoxide and hydrogen which are initially present in the reaction mixture can be varied over a wide range. In general, the mole ratio of carbon monoxide to hydrogen is in the range of between about 30:1 and about 1:30, preferably between about 15:1 and about 1:15 and most preferably, between about 10:1 and about 1:10. It is to be understood, however, that molar ratios outside the stated broad range may be employed. Substances or reaction mixtures which form carbon monoxide and hydrogen under the reaction conditions may be employed in lieu of the mixtures of carbon monoxide and hydrogen. For example, one may use mixtures containing carbon dioxide and hydrogen, mixtures of carbon dioxide, carbon monoxide and hydrogen, as well as mixtures of steam and carbon monoxide. The intended purpose is to provide enough carbon monoxide in combination with hydrogen in the homogenous liquid phase reaction mixture to produce the ester product The manner in which the carbon monoxide and hydrogen are provided in the homogenous liquid phase reaction mixture is not important in the practice of this invention, as long as they are present in a sufficient quantity to effect the production of the desired ester products.

The process of this invention can be carried out in a batch, semi-continuous or continuous manner. The reaction may be conducted in a single reaction zone or in a plurality of reaction zones, in series or in parallel. The reaction may be conducted intermittently or continuously in an elongated tubular zone or a series of such zones. The material of construction of the equipment should be such so as to be inert during the reaction. The equipment should also be able to withstand the reaction temperatures and pressures. The reaction zone can be fitted with internal and/or external heat exchangers to control undue temperature fluctuations, or to prevent possible "run-away" reaction temperatures caused by the exothermic nature of the reaction. In a preferred embodiment of the present invention, agitation means to ensure complete mixing of the reaction mixture should be employed. Mixing induced by vibration, shaker, stirrer, rotating, oscillation, etc. are all illustrative of the types of agitation means which are contemplated herein. Such agitation means are available and well known to the art.

The catalyst may be initially introduced into the reaction zone batchwise. Alternatively, the catalyst may be introduced into the reaction zone continuously or intermittently during the course of the synthesis reaction. Means to introduce the reactants into the reaction zone during the course of the reaction and/or means to adjust the reactants in the reaction zone during the reaction, either intermittently or continuously, can be conveniently utilized in the process to maintain the desired molor ratios of reactants and to maintain the partial pressures exerted by the reactants.

The operative conditions of the present process may be adjusted to optimize the conversion of the desired product and/or the economics of the process. Most preferably, to improve ethylene glycol ester production, the volume concentration of methyl ester, ethylene glycol ester and water is maintained at less than about 30 percent, as described in copending application Ser. No. 971,750 filed on an even date herewith.

In a continuous process, for example, it is preferred to operate at relatively low conversions, and it is desirable to recirculate unreacted mixtures of carbon monoxide and hydrogen to the reactor with or without makeup carbon monoxide and hydrogen. Recovery of the desired product can be achieved by methods well-known in the art, such as by distillation, fractionation, extraction, and the like. Typically, in carrying out the process, the product contained in the homogeneous liquid phase reaction would be withdrawn from the reaction zone and distilled to recover desired product. Thereafter, if desired, a fraction comprising ruthenium catalyst components generally contained in the by-products and/or solvent or acyl compound, can by recycled to the reaction zone. All or a portion of such a fraction can be removed for recovery or regeneration of the ruthenium catalyst. Fresh ruthenium compound can be intermittently added to the reaction stream or it can be added directly to the reaction zone, to replenish any ruthenium catalyst which is lost in the process.

In another aspect of this invention a novel ruthenium carbonyl complex catalyst is described. This novel catalyst is capable of producing methyl and ethylene glycol esters by reacting carbon monoxide, hydrogen and acyl compound. This catalyst is defined as a ruthenium carbonyl complex which will produce methyl ester and ethylene glycol ester as the predominant products when existing in a homogenous liquid phase mixture in the presence of carbon monoxide, hydrogen and acyl compound, when the mixture is maintained af a temperature of between about 50 ° C. and about 400° C. and a pressure of between about 500 psia (36.535 kg/cm$^2$) and about 12,500 psia (878.8 kg/cm$^2$) As pointed out previously, the ruthenium carbonyl complex catalytic species is not known. The ruthenium carbonyl compounds supplied to the homogenous liquid phase reaction mixture are not themselves catalysts unless hydrogen, carbon monoxide and acyl compound are present and the reaction conditions, as previously described, are maintained.

Therefore, the aforementioned description of the acyl compound, homogenous liquid phase reaction mixture, temperature, pressure, and the characterization of the products of the reaction all are important in and bear a relationship to the nature of the novel catalyst of this invention.

Although this invention has been described with respect to a number of details, it is not intended that this invention should be limited thereby. The examples which follow are intended solely to illustrate the most favorable embodiments of this invention which to date have been determined and are not intended in any way to limit the scope and the intent of this invention.

EXAMPLE 1

A 500 ml stainless steel bomb reactor containing a removable glass liner was charged with a mixture of 0.50 g $Ru_3(CO)_{12}$ in 50 ml of glacial acetic acid. Equimolar amounts of carbon monoxide and hydrogen were then added to the reactor to attain a pressure therein of 3000 psi at 25° C. The reactor was rocked and the contents heated to 230° C. and maintained at this temperature for two hours with continued rocking of the reactor. The reactor was then cooled and vented. The contents of the reactor were removed and analyzed by gas chromatography. This analysis showed that the following products were produced: 3.25 g methyl acetate, 1.71 g ethyl acetate (from reduction of acetic acid), and 0.17 g ethylene glycol diacetate.

EXAMPLE 2

The procedure of Example 1 was exactly repeated except that the reactor was charged with a mixture of 0.94 g of Ru(acetyl acetonate)$_3$ in 50 ml of glacial acetic acid instead of $Ru_3(CO)_{12}$ in 50 ml of glacial acetic acid. Analysis by gas chromatography showed that the following products were produced: 2.77 g methyl acetate and 0.16 g ethylene glycol diacetate. Ethyl acetate was also observed.

EXAMPLE 3

The procedure of Example 1 was exactly repeated except that a mixture of 0.5 g $Ru_3(CO)_{12}$ in 25 ml of glacial acetic acid and 25 ml ethyl acetate was used instead of $Ru_3(CO)_{12}$ in 50 ml of glacial acetic acid. Analysis by gas chromatography showed that the following products were produced: 5.51 g methyl acetate and 0.06 g ethylene gylcol diacetate.

EXAMPLE 4

A reactor, as described in Example 1, was charged with a mixture of 0.50 g $Ru(CO)_{12}$ in 50 ml of glacial acetic acid. Equimolar amounts of carbon monoxide and hydrogen were then added to the reactor to attain a pressure therein of 3700 psi at 25° C. The reactor was rocked and the contents heated to 230° C. and maintained at this temperature for two hours with continued rocking of the reactor. The reactor was cooled and vented. The contents cf the reactor were removed and analyzed by gas chromatography. This analysis showed that the following products were produced: 4.22 g methyl acetate and 0.24 g ethylene glycol diacetate. Ethyl acetate was also observed.

EXAMPLES 5 TO 8

The procedure of Example 1 was exactly repeated except that glacial acetic acid and sulfolane were used in amounts as indicated in Table I in place of acetic acid.

The ethylene glycol diacetate and methyl acetate products produced are as shown in Table I.

TABLE I

| Example | Solvent | | Products | |
|---|---|---|---|---|
| | Acetic acid, ml | Sulfolane, ml | Ethylene glycol diacetate, g | Methyl acetate, g |
| 1 | 50 | 0 | 0.184 | 3.45 |
| 5 | 40 | 10 | 0.249 | 4.00 |
| 6 | 25 | 25 | 0.193 | 3.20 |
| 7 | 12.5 | 37.5 | 0.114 | 1.21 |
| 8 | 0 | 50 | — | (0.57 g CH$_3$OH) |

EXAMPLE 9

The procedure of Example 1 was exactly repeated except that a mixture of 37.5 ml of glacial acid and 12.5 g of dimethylsulfone was used instead of 50 ml of glacial acetic acid. Product anaylsis showed 0.22 g of ethylene glycol diacetate was formed Methyl acetate and ethyl acetate were also observed.

EXAMPLE 10

The procedure of Example 1 was exactly repeated except that a mixture of 40 ml of glacial acetic acid and 10 ml of butyrolactone was used instead of 50 ml of glacial acetic acid. Product analysis showed 0.23 g of ethylene glycol diacetate was formed. Methyl acetate and ethyl acetate were also produced.

EXAMPLE 11

The procedure of Example 1 was exactly repeated except that a mixture of 40 ml of glacial acetic acid and 10 ml of tri-n-butylphosphine oxide was used instead of 50 ml of glacial acetic acid. Product analysis showed 0.193 g of ethylene glycol diacetate and 3.47 g of methyl acetate. Ethyl acetate was also formed.

The data of Examples 1, and 9 to 11 are summarized in Table II as follows:

TABLE II

| Example | Solvent | | Product |
|---|---|---|---|
| | Acetic acid, ml | Co-Solvent, ml | Ethylene glycol diacetate, g |
| 1 | 50 | 0 | |
| 9 | 37.5 | Dimethylsulfone (12.5 g) | 0.22 |
| 10 | 40 | Butyrolactone (10) | 0.23 |
| 11 | 40 | tri-n-butylphosphine oxide (10) | 0.193 |

What is claimed is:

1. The process for producing methyl and ethylene gylcol esters which comprises reacting carbon monoxide and hydrogen in a homogenous liquid phase mixture comprising a ruthenium carbonyl complex, an acyl compund selected from the group consisting of a carboxylic acid, a carboxylic acid anhydride and mixtures thereof, and a cosolvent which in combination with the acyl compound increases the yield of said ethylene glycol esters at a temperature of between about 50° C. and about 400° C. and a pressure of between about 500 psia. and about 12,500 psia. for a period of time sufficient to produce such esters as the predominant product.

2. The process as in claim 1 wherein the co-solvent is a sulfone, a phosphine oxide or a lactone.

* * * * *